(12) United States Patent
Shepard

(10) Patent No.: US 6,516,084 B2
(45) Date of Patent: Feb. 4, 2003

(54) TEMPORAL NOISE REDUCTION, COMPRESSION AND ANALYSIS OF THERMOGRAPHIC IMAGE DATA SEQUENCES

(75) Inventor: Steven M. Shepard, Southfield, MI (US)

(73) Assignee: Thermal Wave Imaging, Inc., Ferndale, MI (US)

( * ) Notice: Subject to any disclaimer, the term of this patent is extended or adjusted under 35 U.S.C. 154(b) by 156 days.

(21) Appl. No.: 09/729,617

(22) Filed: Dec. 4, 2000

(65) Prior Publication Data

US 2002/0044679 A1 Apr. 18, 2002

Related U.S. Application Data

(60) Provisional application No. 60/168,556, filed on Dec. 2, 1999, and provisional application No. 60/175,792, filed on Jan. 12, 2000.

(51) Int. Cl.$^7$ ................................................. G06K 9/00
(52) U.S. Cl. ........................ 382/141; 250/332; 374/10
(58) Field of Search ................................ 382/141, 143, 382/149, 152; 250/330, 332, 339.02, 339.14, 341.1, 341.6, 358.1; 356/51; 374/5, 10, 120, 121, 124, 137; 209/577; 348/86, 125; 700/95, 212

(56) References Cited

U.S. PATENT DOCUMENTS

| | | | | |
|---|---|---|---|---|
| 4,719,350 A | * | 1/1988 | Alm ............................ | 250/330 |
| 5,032,727 A | * | 7/1991 | Cox, Jr. et al. .............. | 250/330 |
| 5,631,465 A | * | 5/1997 | Shepard ....................... | 250/330 |
| 5,711,603 A | * | 1/1998 | Ringermacher et al. ....... | 374/5 |
| 5,939,721 A | * | 8/1999 | Jacobsen et al. ............. | 250/330 |
| 5,963,662 A | * | 10/1999 | Vachtseuanos ............... | 382/150 |
| 6,367,969 B1 | * | 4/2002 | Ringermacher et al. ....... | 374/7 |

* cited by examiner

*Primary Examiner*—Samir Ahmed
(74) *Attorney, Agent, or Firm*—Rader, Fishman & Grauer PLLC

(57) ABSTRACT

A method and system for non-destructive, reference-free thermographic detection of sub-surface defects uses an infrared camera to capture images of a sample that has been heated and allow to cool to equilibrium temperature. The temperature-time data obtained for each pixel in each image is converted into the logarithmic domain and a least squares fit is conducted on the data to generate a polynomial expression corresponding to the temperature-time data for a given pixel. This polynomial expression can be transformed into the original time domain to obtain temperature-time data with improved signal-to-noise characteristics. Defects can be detected by observing the zero-crossing characteristic of the second derivative of the polynomial.

25 Claims, 3 Drawing Sheets

TEMPORAL NOISE REDUCTION, COMPRESSION AND ANALYSIS OF THERMOGRAPHIC IMAGE DATA SEQUENCES

REFERENCE TO RELATED APPLICATIONS

This application claims the benefit of U.S. Provisional Application No. 60/168,556, filed Dec. 2, 1999, and U.S. Provisional Application No. 60/175,792, filed Jan. 12, 2000, the disclosures of which are incorporated by reference herein in their entirety.

TECHNICAL FIELD

The present invention relates to the field of non-destructive evaluation of defects in a solid sample, and more particularly to a method and system for analyzing thermographic image data to detect sub-surface defects.

BACKGROUND OF THE INVENTION

Non-destructive evaluation of samples for sub-surface defects can be used to check samples for weld integrity, delamination, and other structural defects that are not visible from observing the surface of the sample. Active thermography has been viewed as one option for non-destructive testing. Generally, active thermography involves heating or cooling the sample to create a difference between the sample temperature and the ambient temperature and then observing the surface temperature of the sample as it returns to ambient temperature. For purposes of illustration only, the description will focus on the heating example, where the sample is heated via any means (e.g., flashlamps, heat lamps, forced hot air, hot air guns, electrical current, ultrasonic excitation, etc.) and then the allowed to cool. In this type of process, the subsequent cooling is monitored using an infrared camera to detect any anomalies in the cooling behavior, which would be caused by sub-surface defects (e.g., voids, delaminations, inclusions, etc.) blocking the diffusion of heat from the sample surface to the sample's interior. More particularly, these defects cause the surface immediately above the defect to cool at a different rate that the surrounding defect-free areas.

As the sample cools, the infrared camera monitors and records an image sequence indicating the surface temperature, thereby creating a record of the changes in the surface temperature over time. The sub-surface defects can therefore be observed by viewing the output of the infrared camera through a display device or by capturing individual frames at selected times after the sample has been heated. This method of visual defect identification tends to be subjective, however, and is not suitable for automation of the defect detection process. Further, it is not possible to measure the depth of the defects simply by viewing the infrared images.

There have been attempts to determine the depth of a defect via processing and analysis of the data from the infrared camera and also to automate the defect detection process. In some cases, the data from the infrared camera is transferred to a computer for processing and analysis to detect variations in the cooling behavior or to perform mathematical operations on the data to determine the depth of the sub-surface defect or other defect properties. These types of calculations, however, often require expensive low noise, high-speed digital infrared cameras. Further, the cumbersome nature of having a computer attached to the camera for conducting calculations makes the combination impractical for applications outside of a laboratory, such as field inspections. Also, infrared data sequences of thermal decay typically used in non-destructive testing tend to be difficult to manipulate mathematically due to low signal-to-noise ratios and large dynamic range and also requires a great deal of storage space.

One attempt at automating the defect detection process involves analyzing the contrast between each pixel in the image and a reference pixel or pixel group to generate a curve representing the amount of contrast between each pixel and the reference. This method requires identification of a reference point on the sample. The reference point can be a defect-free area of the sample, a separate defect-free sample that is placed in the camera's field of view, or the mean of the entire field of view of the camera. The temperature-time history of this reference pixel or pixel group is subtracted from each pixel in the image to generate a contrast vs. time plot.

Any large differences between any given pixel and the reference indicates the presence of a defect and will exhibit itself as a peak in the plot. The contrast vs. time plot can be measured with respect to the time at which the peak occurs, the time at which a maximum ascending slope occurs, and/or a moment of the curve for each pixel. Other options, such as generating and displaying the contrast vs. time plot with a reference plot and checking the point at which the two plots separate, is also an option.

Contrast-based methods tend to be flawed, however. In addition to the data storage problems noted above due to the large size of the infrared image data files, contrast-based methods require the identification of a defect-free region on the sample as a reference point. This requirement is often not realistic for some samples if, for example, the size of the defect is larger than the infrared camera's field of view. In such a case, there is no defect-free area available that can act as a reference for a given region. Further, if the entire sample exhibits a defect (e.g., a large delamination running underneath the entire surface of the sample), there is no contrast between any region of the sample because the whole sample is equally or nearly equally defective.

Contrast-based methods that rely on the mean of the entire field of view as a reference have also been used, but this method assumes that the defect area in the field is small enough so that it will not appreciably affect the mean. If a defect or group of defects occupy a large portion of the field of view, the contrast method will be ineffective because the mean value will be influenced to a large degree by the defects, reducing any appreciable difference between the defect area and the mean when the contrast value is calculated.

Regardless of the specific reference value used in detecting defects, the results obtained using contrast-based methods depends strongly on the choice of reference region on the sample. More particularly, the results obtained in contrast-based methods can be adjusted by simply changing the location of the reference region.

Further, in evaluating the results from both the contrast-based methods and the data obtained directly from the infrared camera, identifying the time at which a peak slope occurs (indicating the presence of a defect) may be difficult because the signals are often inherently noisy, requiring the defect detection system to discriminate pixels associated with defects from noisy pixels.

There is a need for a non-destructive defect detection system and method that reduces the size and complexity of the temperature-time history of image data without sacrificing its usefulness in detecting the location and physical characteristics of sub-surface defects.

There is also a need for a non-destructive defect detection system that does not require obtaining a reference value to detect defects by locating areas in which there is a contrast between the reference and the sample being evaluated.

There is further a need to improve the signal-to-noise ratio of the camera output without sacrificing spatial resolution.

SUMMARY OF THE INVENTION

Accordingly, the present invention is directed to a system and method for non-destructive detection of subsurface defects that avoids the problems encountered by currently known systems. The inventive system and method determines the response of a monotonically changing characteristic, such as temperature, of a sample over time and captures a plurality of images as the sample characteristic changes. The images are used to generate a data array for each pixel in the images. The data array corresponds to a logarithm of the pixel amplitude and a logarithm of a given time so that a plot of monotonically changing characteristic will be roughly linear.

A polynomial is then fitted to the data array. The polynomial contains at least two polynomial coefficients, and typically from five to seven polynomial coefficients. These coefficients are analyzed instead of the raw data in the data array, simplifying mathematical manipulation of the data. Because the system preferably stores and evaluates the coefficients representing the sample characteristic, and not the sample characteristic data itself, the amount of data that needs to be stored is greatly reduced. In one embodiment, defects can be detected by checking whether the second derivative of the polynomial has a zero crossing. Further, the polynomial data has a higher signal-to-noise ratio than the original data, allowing the polynomial data to serve as a less noisy substitute for the raw image data when the polynomial data is converted from the logarithmic domain back into the linear domain.

DETAILED DESCRIPTION OF THE PREFERRED EMBODIMENTS

As a general matter, the present invention detects subsurface defects using an infrared camera by observing and analyzing selected characteristics of a thermal decay process. The basic foundation in which the inventive system operates assumes that the field of view is limited to the sample of interest. Further, the inventive system and method recognizes that the heated region of the sample cools monotonically after the heater is removed until the sample reaches equilibrium with its surroundings, that the thermal response of any point on the sample surface during the time interval immediately after heating decays in such a manner that the natural logarithm of the temperature-time response of the sample as it cools is a function that can be approximated by a straight line.

Figure 1:
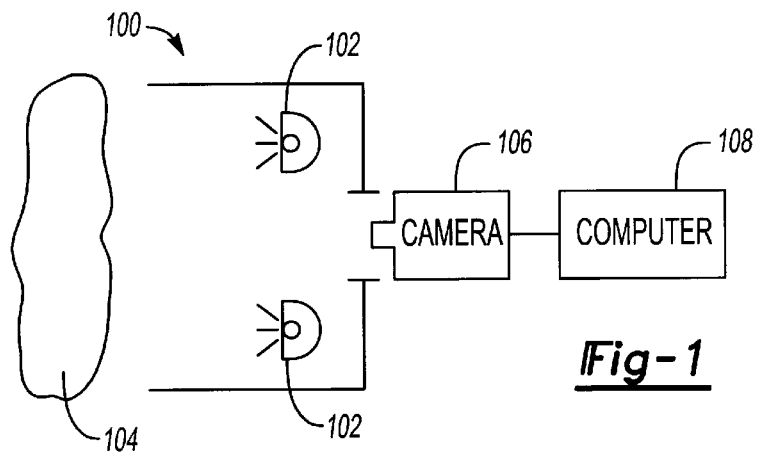
FIG. 1 is a representative diagram of one embodiment of a system implementing the claimed invention.
Figure 2:
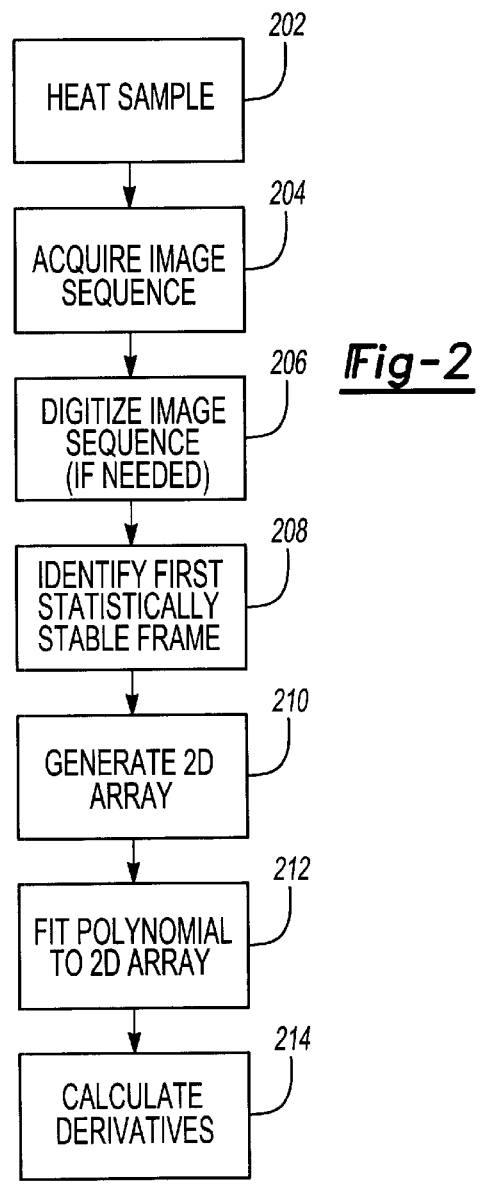
FIG. 2 is a flowchart illustrating an embodiment of the inventive process.

FIG. 1 illustrates one possible embodiment of the system used to carry out the invention, while FIG. 2 is a flowchart illustrating one embodiment of the inventive process. Referring first to FIG. 1, a system 100 for obtaining the data to be analyzed in the inventive method includes at least one heat source 102, and preferably a pulsed heat source, that heats a sample 104 to be evaluated with a pulse. The heat source itself can be any source, such as flashlamps, heat lamps, electric current, heated air, electromagnetic induction, ultrasonic energy, etc., but the specific choice of heat source does not matter for purposes of the invention as long as there is a heating of the sample and then a monotonic, exponential decrease in the sample's temperature. An infrared camera 106 obtains images of the sample, preferably in real time, and is coupled to a computer 108 having digital image acquisition or analog frame-grabbing capabilities to convert the data from the infrared camera 106 to a format that can be analyzed and mathematically manipulated by the computer 108. Note that the computer 108 does not necessarily need to be separate from the camera 106 and that the functions in the computer 108 can be incorporated into the camera itself as, for example, an on-board chip.

Referring now to the flowchart in FIG. 2, the inventive method 200 first involves heating the sample at step 202 and starting acquisition of an image sequence of the sample at step 204. The image sequence can be stored in computer memory, videotape, or any other electronic storage means. Digital data corresponding to the image sequence is then transferred to a computer or dedicated hardware for mathematical analysis; note that if the data is analog data, it is first digitized at step 206 before it is transferred. The length of the image sequence may depend on the type of material being inspected and the depth at which suspected defects are located; if the material has low thermal conductivity and/or if the suspected defects are relatively deep inside the sample, the image sequence may be lengthened. In one embodiment, a typical image sequence from an infrared camera operating at 60 frames per second will contain several hundred frames. In other cases, the image sequence may contain as many as several thousands of frames. The time over which the data acquisition step 206 takes place can range over several seconds as the sample temperature returns to equilibrium, but the specific length of time will vary depending on the thermal properties of the sample. Further, the image sequence can be generated over any time between the heating flash and the end of the image sequence to be created, independent of the sampling rate of the infrared camera 106.

The frames are then inspected at step 208 to locate the first frame that is statistically stable, that is, the first frame for which the change in standard deviation is less than a predetermined threshold value. The reason for this step is because the first several frames obtained immediately after the sample is heated may display non-linear behavior. These frames can be detected due to large changes in the standard deviation between consecutive frames; during normal cooling conditions, the changes in standard deviation are normally relatively small. Once the statistically unstable frames have been identified, they are removed from consideration, leaving the stable frames available for analysis.

Figure 3A:
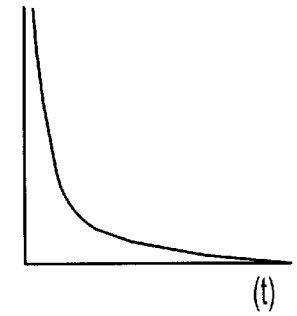
FIGS. 3a and 3b are graphs illustrating a temperature-time characteristic in a linear domain and in a logarithmic domain.
Figure 3B:
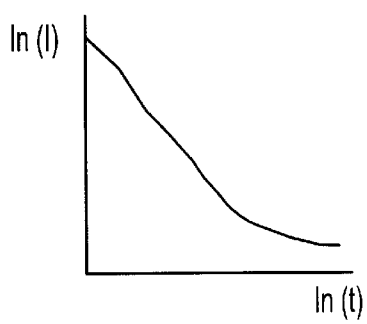

For each individual pixel in each stable frame, the computer generates a two-dimensional array at step 210 which is illustrated in the example in FIG. 3b. The temperature-time characteristic of a point on the sample will exhibit a monotonic decay, as can be seen in FIG. 3a. To simplify analysis of the temperature-time characteristic, the array generated by the invention includes the natural logarithm of the amplitude of the pixel (which corresponds to the temperature at that point of the sample) and the natural logarithm of the time at which that image was taken. The time of the first entry in the array coincides with the first statistically stable frame, as identified at step 208. The array associated with each pixel and each time will exhibit generally linear behavior, with a smaller dynamic range and a higher signal-to-noise ratio, as can be seen in FIG. 3b.

Next, a least squares fit is conducted for each two-dimensional array using an nth order polynomial at step 212. Note that the invention fits a polynomial to the natural logarithm of the temperature-time characteristic and not to the actual temperature-time characteristic in the linear domain. The reason is because the dynamic range of the raw temperature-time data is too large for accurate polynomial curve fitting, and any curve that is fitted to the actual temperature-time characteristic tends to fit poorly and to oscillate at low signal amplitudes. The resulting function for the amplitude for a given pixel at location i,j (i=row, j=column) is defined as:

$$ln[I_{ij}(t)] = a_0 + a_1 ln(t) + a_2[ln(t)]^2 + \ldots + a_n[ln(t)]^n \quad (1)$$

Figure 4:
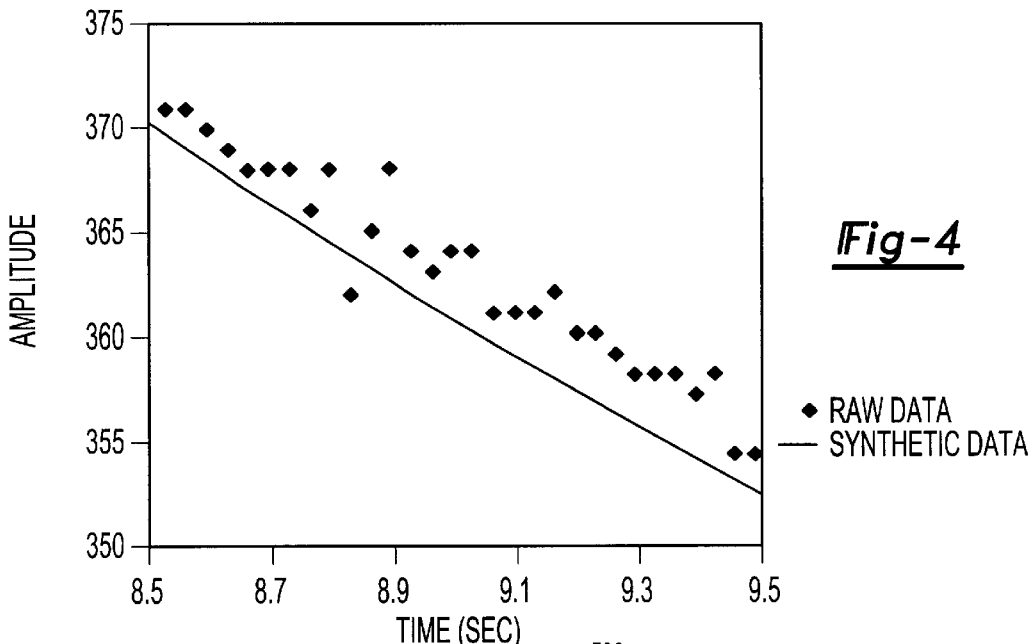
FIG. 4 is a graph illustrating one example of how the inventive system fits a polynomial to raw data according to one embodiment of the invention.

As can be seen from Equation 1, the resulting polynomial from step 212 is a continuous function obtained from the discrete data in the two-dimensional array, thereby allowing a user to obtain pixel amplitude values for time values that fall between the actual frame acquisitions. An example of the resulting temporal noise reduction and spatial noise reduction from the least squares fit is shown in FIGS. 4a and 4b, respectively. FIG. 4a compares the raw and synthetic ln(intensity) versus ln(time) data for a sample using a sixth order polynomial, while FIG. 4b compares the raw and synthetic intensity. As can be seen in both figures, the order of the polynomial is preferably relatively low and limited to an order (e.g., seventh order) that avoids replication of the high-frequency noise in the infrared camera signal along with the desired data.

Once the polynomial has been generated at step 212, each pixel is represented by an array of n polynomial coefficients, which will typically be seven coefficients or less, making it unnecessary to store the actual data sequence, which can be several hundreds or even thousands of frames, generated by the infrared camera. Because the polynomial representation includes only an array of coefficients, and because the polynomial representation of the pixel temperature-time characteristic is independent of the length of the data sequence, the amount of data that needs to be stored for any given pixel is greatly reduced by the polynomial representation and much simpler to manipulate mathematically than the raw camera data. The file size for storing the pixel data is independent of the number of images taken by the camera, further reducing the memory needed to store the image data. For example, in one embodiment, the file size is the number of pixels being imaged multiplied by the number of coefficients in the polynomial muliped by the number of bytes per coefficient, regardless of the Once the polynomial representation is obtained via the natural log transformation of the camera data, the representation can be transformed back into the original temperature-time domain by performing the following operation:

$$I_{ij}(t) = \exp\{ln([I_{ij}(t)])\} \quad (2)$$
$$= \exp\{[a_0 + a_1 ln(t) + a_2[ln(t)]^2 + \ldots + a_n[ln(t)]^n\}$$

The function that results from this operation replicates the original temperature-time data from the camera, but it will not contain the high-frequency noise that is present in the raw camera data. This re-transformed data can be used instead of the raw data for analysis purposes. Because the polynomial suppresses the small, high-frequency noise variations that often occur after a certain time period has elapsed while preserving the low frequency variations caused by thermal events, the expression that results from transforming the polynomial function from the logarithmic domain back to the linear domain will be a synthetic temperature-time curve that has a significantly higher signal to noise ratio than the original signal, making it more suitable for signal analysis.

To obtain additional information about the data sequence, the first and second derivatives of the polynomial can be optionally calculated at step 214. More particularly, given the expression:

$$f(t) = \exp\left[\sum_{i=0}^{N} a_1[ln(t)]^i\right] \quad (3)$$

the first derivative can be expressed as:

$$f'(t) = t^{-1}[\Sigma a_i[ln(t)]^{i-1}]f(t) \quad (4)$$

and the second derivative can be expressed as:

$$f''(t) = t^{-1}[\Sigma a_1[ln(t)]^{i-1}]^2 f(t) + t^{-2}\{[\Sigma i(i-1)a_i[ln(t)]^{i-2}] - [a_i[ln(t)]^{i-1}]\}f(t) \quad (5)$$

Images of the first and second derivatives can be generated from Equations 4 and 5 through any means, if desired, by entering time information into the polynomial, the first derivative, and/or the second derivative. Note that because the derivatives of the image data are calculated analytically rather than by fitting a straight line to the tangent of the noisy image data, the results obtained from the calculated derivatives yields more accurate results than attempts to compute the average over many noisy data points. Further, analytical calculation of the first and second derivatives yields results that are true instantaneous derivatives rather than differentials over an interval spanning several image frames.

Because the invention focuses on differentiating and analyzing the polynomial function instead of the raw image data, obtaining information about the thermal characteristics of the sample is much simpler because differentiating the polynomial representation is less computationally complex than differentiating a noisy signal. More particularly, operating on the coefficients of the polynomial, and not on the original data, eliminates the need to manipulate hundreds or even thousands of separate images, greatly improving the speed in which the image data can be analyzed. Also, because the first and second derivatives are obtained by manipulating the polynomial expression rather than conducting linear regression or curve fitting, the derivatives do not themselves contribute any noise to the final result. Further, because the invention uses noise-reduced, analytically differentiated data obtained from logarithmically scaled data, the noise reduction provided by the invention allows more accurate detection of deeper and weaker defects as well as large defects encompassing the entire field of view.

For purposes of defect detection, only the polynomial argument (Equation 1) in the exponential expression (Equation 2) above, and not the entire polynomial, may be used to identify sub-surface defects as an alternative to using the entire exponential expression. The first and second derivatives of the polynomial can be applied to the time history of each pixel (i.e. time information can be entered into the first and second derivatives to obtain numerical values) to generate an image signal with a better signal-to-noise ratio than the original polynomial expression, thereby creating a clearer image.

Although it may be useful in some cases to calculate the complete second derivative of Equation 2 (e.g., if the user wishes to create a synthetic sequence of second derivative images), automated defect detection can be conducted sufficiently by differentiating Equation 1, that is, by calculating a synthetic derivative based on only the polynomial argument rather than on the entire function.

The inventive system and method of generating polynomial equations from the image data may also be used to generate a contrast curve by identifying a defect-free reference region of the sample or using a separate reference sample and deriving the polynomial equation associated with the reference, if desired. A contrast curve can then be generated by subtracting the polynomial expression for the reference from the polynomial expression for each pixel; a large difference between the two would indicate the presence of a defect. Note that although this application of the invention uses a reference region or sample, it is wholly optional.

Once steps 210 through 214 have been conducted for every pixel at a given time t, an image representation of the behavior of the sample at that time can be scaled to match the dynamic range of the display device. This scaling operation can be conducting using any common statistical scaling algorithm.

The image or images based on the polynomial and/or its derivatives can be displayed on an output device, such as on a computer display. The display can be a single image at a selected time t or a sequence of images shown as a movie. The temporal resolution of the movie can be different than the actual data acquisition frame rate, if desired, to show the changes in the sample temperature more clearly; this can be conducted easily because the derived polynomial is a continuous function, as noted above.

The particular manner in which the sample is thermally excited and in which the data is obtained for polynomial fitting is not crucial to the invention and can be obtained in any manner. For example, the data can be obtained from temperature-time data in an image that is scanned (e.g., systems that acquire image data as the sample is moved relative to a heat source and an IR camera at a constant velocity, systems that move the camera and heat source relative to the sample, etc.).

Figure 5:
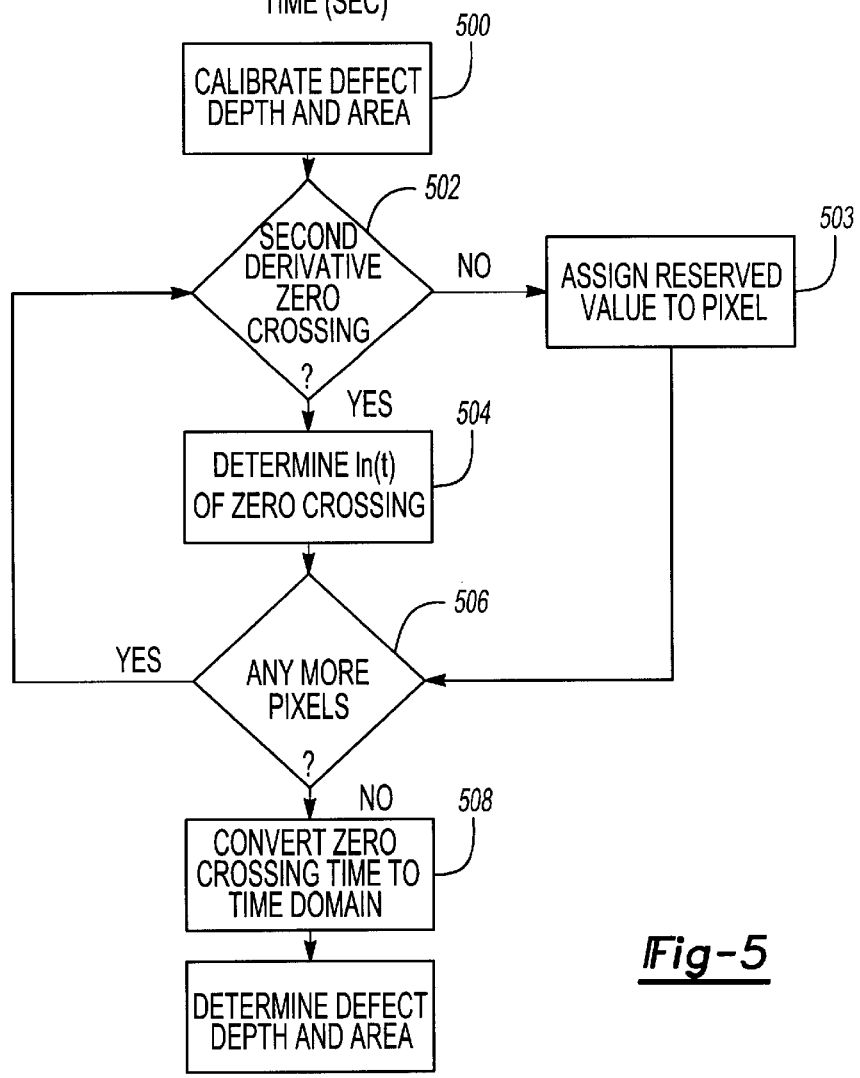
FIG. 5 is a flowchart illustrating one method in which the inventive system detects defects in a sample.

FIG. 5 is a flowchart illustrating how the generated polynomial is used in defect detection. Before the actual measurement takes place, the system can be calibrated to determine defect depth and area at step 500. If a depth of a particular defect in the sample is known, this defect can be used to calibrate the defect map according to the relationship:

$$\text{Depth} = A(t_{zerocross})^{1/2} \quad (6)$$

By using a known depth and known corresponding zero crossing time, the constant A can be determined from the above equation.

Spatial calibration can also be conducted by placing an object having known dimensions in the camera's field of view and then counting the number of pixels required to create the image of the object. This information generates a value corresponding to the area covered by a single pixel at a fixed distance from the camera.

As explained above and shown in FIG. 2, the system first generates a polynomial expression and a first and a second derivative for each pixel at each point in time at steps 212 and 214. Next, for each pixel, the computer 108 determines the logarithm of the time at which the earliest zero crossing for each pixel occurs at steps 502 and 504. If no such time exists, then the pixel is considered defect-free and the pixel is assigned a reserved value corresponding to a particular color or color group at step 503. The process then repeats for all of the pixels in the image at step 506. Once the second derivative for all of the pixels have been obtained for the entire data sequence, the zero crossing times and/or the reserved values are placed in a two dimensional array, creating a defect map of the data sequence.

Once the defect map has been created, the logarithm of the zero crossing time is converted back to the time domain at step 508 by taking its exponential as follows:

$$t_{zerocross} = \exp(ln(t_{zerocross})) \quad (7)$$

Figure 7:
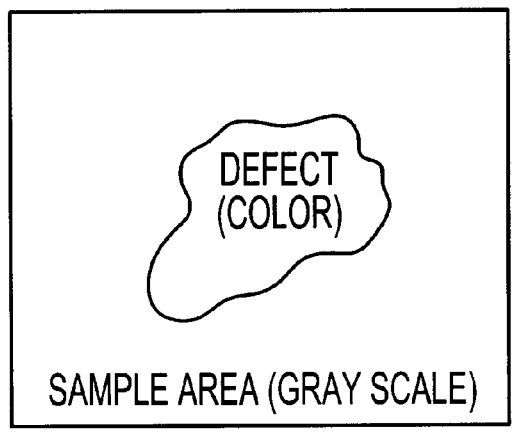
FIG. 7 is a representative diagram of a defect map generated by the inventive system.

The exponential of the defect map array can then be displayed as an image by, for example, mapping the array to a mapped color palette where selected colors are assigned to numerical values. Pixels that do not have any zero crossings may be mapped to a selected color or displayed at a gray scale value that is proportional to the pixel amplitude at a particular time after flash heating. Preferably, the resultant defect map array will show the defects in colors that correspond to the depth of the defect and that are superimposed on a uniform selected color or gray scale image of the sample showing the normal sub-surface structure of the sample. A representative example of such a defect map is shown in FIG. 7.

If the system has been calibrated according to step 500 above, the invention can then determine the defect depth and area at step 510. To determine the defect depth, the system uses the constant A corresponding to the material composition of the sample. Constant A is calculated from the temperature-time information of a defect having known dimensions (i.e., A can be readily calculated from Equation 6 if the zero-crossing time and the depth are known for a reference defect). To determine the defect area, the total number of pixels having zero-crossing values are counted and multiplied by the single pixel area. The defect area value can be significant because the criteria for rejecting a sample is often based on the defect area.

As can be seen above, no reference value is required to detect sub-surface defects. As a result, the invention can detect defects even in a sample that has a defect spanning the entire sample.

The above process can be used to pre-process any images from an infrared camera for further analysis, such as peak slope or peak contrast time measurements, breakpoint analysis, pulse phase lock-in, etc. The pre-processing steps described above generate an image signal with much of its temporal noise removed, yielding more accurate results in any additional processes.

Although the above examples focus on using a single polynomial expression to describe the temperature-time characteristic for a given sample, more than one polynomial expression may be desired to address the thermal behavior at the extremes of the temperature time characteristic and prevent the extremes from skewing the analysis of the temperature-time behavior of the sample. More particularly, with reference to FIG. 6, the polynomial fit when using one polynomial may be adversely affected by the temperature-time curve behavior at the very early and very late stages. As noted above, in the early stages immediately after flash heating, the infrared camera data may become briefly saturated and may initially display non-linear behavior that does not reflect the thermal characteristics of the sample accurately. In the late stages, the temperature-time characteristic of the sample tends to be weaker and therefore more susceptible to noise and/or temperature fluctuations due to convection or stray radiation.

Figure 6:
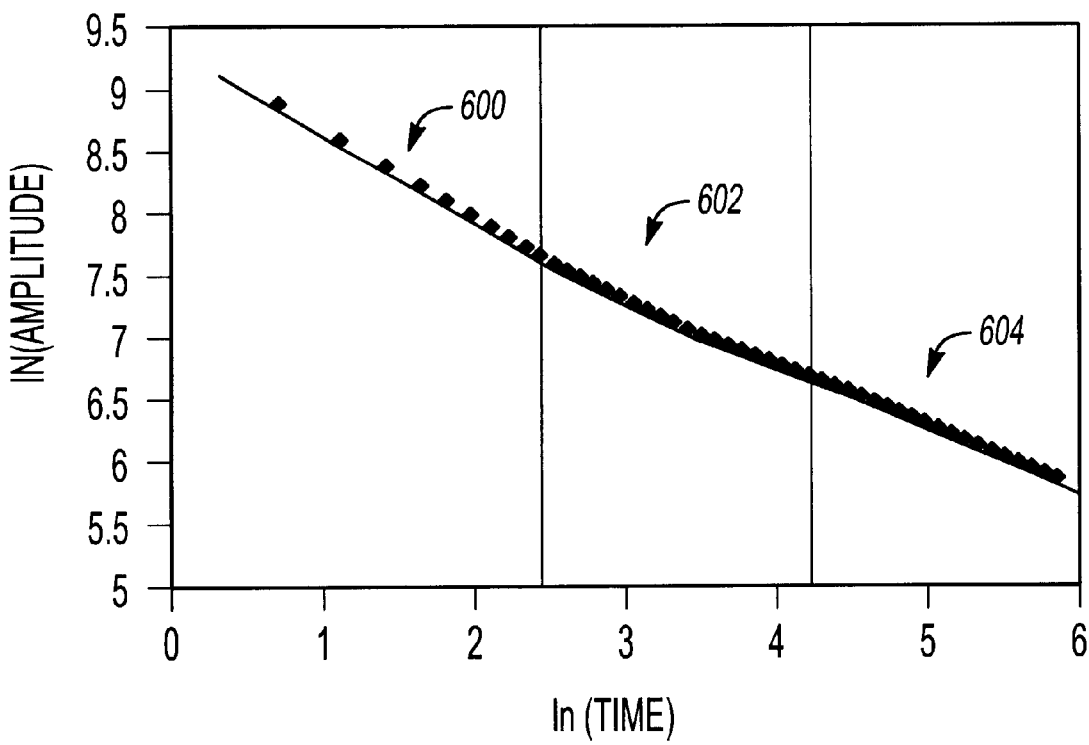
FIG. 6 is a graph illustrating an example of how the inventive system fits a polynomial to raw data according to another embodiment of the invention.

To prevent the extreme portions of the temperature-time characteristic from affecting the results in the central region, the example shown in FIG. 6 uses more than one polynomial equation to describe the complete temperature-time history of each pixel. In the example shown in the Figure, the temperature-time characteristic is divided into early, intermediate, and late behavior regions, 600, 602 and 604 respectively, each of which exhibit slightly different temporal behavior, and each region is described using a different low-order polynomial. When viewed separately, the temperature-time characteristic for each individual region 600, 602, 604 behaves more like a linear function than a single plot of the entire time sequence. As a result, each separate region is more easily approximated by a low-order polynomial than the entire temperature-time plot.

Detecting defects using the polynomial for each region is the same as described above. More particularly, the processor can calculate first and second derivatives of one or more of the polynomials. Further, as explained above, the zero crossing behavior of the second derivative can be used to determine the depth of a defect. Note that the defect depth can also be determined by finding the point in time at which the first derivative of the polynomial deviates from −0.5 by a predetermined threshold. The −0.5 value is generated based on the known temperature characteristic of a semi-infinite solid that has been instantaneously flash-heated, which can be described as:

$$T = \frac{Q}{e(t)^{\frac{1}{2}}} \quad (8)$$

where e is the thermal effusivity of the material (the square root of the product of the density, thermal conductivity and heat capacity), Q is the energy input to the sample by the flash-heating, and t is the elapsed time after flash-heating. When the natural logarithm of the equation is taken, the resulting expression is:

$$ln(T) = (Q/a) - 0.5\, ln(t) \quad (9)$$

As can be seen in the above equation, the natural logarithm of the temperature-time data includes a time-dependent term with a slope of −0.5 that is independent of material properties.

During sample evaluation, the above two equations are useful because a sample will behave like a semi-infinite sample, such that the natural logarithm of the temperature-time data has a slope of −0.5, as heat propagates from the surface into the bulk of the sample until a defect is encountered. If there is a defect in the sample, the temperature-time data will deviate from the −0.5 slope. As a result, the first derivative expression can be used to detect defects by checking whether the first derivative for a given pixel deviates from −0.5 based on this equation.

As a result, the inventive system and method generates a data structure, which is based on the original data sequence obtained from the infrared camera, that is more compact, easier to manipulate mathematically, and less prone to temporal noise than the original data sequence but that still preserves the characteristics that indicate the presence of sub-surface defects. By reducing temporal noise, the inventive system allows relatively inexpensive infrared cameras to be used in the system. Further, because the data generated by the invention is much smaller than the image data obtained from the camera, the stored data can be differentiated and integrated with respect to time more easily than the original data generated by the camera. The analysis and manipulation of the data from the camera can be conducted in an automated fashion, without any user intervention or adjustment.

The inventive system can be used alone or as a pre-processing step in conjunction with other methods for measuring, characterizing, and/or recognizing defects or sample material properties. Although the above-described configuration uses an infrared camera to acquire the data and transfers the data to a computer for further processing, the entire system can be incorporated into the camera itself without a separate computer. Also, although the above example analyzes infrared image data, the inventive system and method can be applied to any data set that is in response to a stimulus that causes a monotonically increasing or decreasing response and where there is no random motion in the field of view in which the data is generated.

It should be understood that various alternatives to the embodiments of the invention described herein may be employed in practicing the invention. It is intended that the following claims define the scope of the invention and that the method and apparatus within the scope of these claims and their equivalents be covered thereby.

What is claimed is:

1. A system for determining a time response to a monotonically changing characteristic of a sample, comprising:
    a camera that obtains a plurality of images of the sample over time, each image having a plurality of pixels, each pixel having an amplitude corresponding to the monotonically changing characteristic of the sample; and
    a processor that receives the plurality of images and generates a data array for at least a portion of the plurality of pixels, the data array corresponding to a logarithm of the pixel amplitude at a given time and a logarithm of the given time, wherein the processor fits a polynomial to at least a portion of the data array, the polynomial having at least one polynomial coefficient, such that each pixel in said portion of plurality of pixels is represented by a coefficient array containing said at least one polynomial coefficient.

2. The system of claim 1, wherein the camera is an infrared camera.

3. The system of claim 1, wherein the processor is in a computer.

4. The system of claim 1, wherein the processor is located on the camera.

5. The system of claim 1, wherein the processor calculates an instantaneous first derivative of the polynomial for a specified time value.

6. The system of claim 5, wherein the processor determines whether the first derivative for each pixel over time deviates from −0.5 by a predetermined threshold.

7. The system of claim 5, wherein the processor calculates an instantaneous second derivative of the polynomial for a specified time value.

8. The system of claim 7, wherein the processor determines whether the second derivative for each pixel has a zero crossing, wherein the presence of the zero crossing indicates a defective pixel and the absence of the zero crossing indicates a defect-free pixel.

9. The system of claim 8, wherein the processor converts the logarithm of the earliest zero crossing time into a linear time domain for defective pixels, assigning a reserved value for defect-free pixels, and using the reserved value and the converted zero crossing time for each pixel to generate a defect map array that uses a first color value for defective pixels and a second color value for defect-free pixels.

10. The system of claim 1, wherein the processor generates a reference polynomial and subtracts the polynomial associated with each pixel in said portion of plurality of pixels from the reference polynomial to generate a contrast curve, wherein a peak in the contrast curve indicates the presence of a subsurface defect.

11. The system of claim 1, wherein the processor fits a first polynomial to a first portion of the data array and a second polynomial to a second portion of the data array.

12. The system of claim 1, wherein the processor divides the data array into an early region, an intermediate region, and a late region and fits a first polynomial to the early region, a second polynomial to the intermediate region, and a third polynomial to the late region.

13. The system of claim 1, further comprising a memory that stores said coefficient array.

14. The system of claim 13, wherein the coefficient array is stored in the memory as a file having a size that is independent of the number of images obtained by the camera.

15. A method for determining a time response to a monotonic change in a characteristic of a sample, comprising the steps of:
obtaining a plurality of images of the sample over time, each image having a plurality of pixels each having an amplitude corresponding to the monotonically changing characteristic of the sample;
generating a data array for each of the plurality of pixels, the data array corresponding to the logarithm of the pixel amplitude at a given time and the logarithm of the given time; and
fitting a polynomial to the data array associated with at least a portion of the plurality of pixels, the polynomial having at least two polynomial coefficients, such that each pixel in said portion of plurality of pixels is represented by a coefficient array containing said at least two polynomial coefficients.

16. The method of claim 15, further comprising the step of calculating an instantaneous first derivative of the polynomial for a specified time value.

17. The method of claim 16, further comprising the step of determining whether the first derivative for each pixel over time deviates from a slope of −0.5.

18. The method of claim 16, further comprising the step of calculating an instantaneous second derivative of the polynomial for a specified time value.

19. The method of claim 18, further comprising the step of determining whether the second derivative for each pixel has a zero crossing, wherein the presence of the zero crossing indicates a defective pixel and the absence of the zero crossing indicates a defect-free pixel.

20. The method of claim 19, further comprising the step of converting the logarithm of the zero crossing time into a linear time domain for defective pixels, assigning a reserved value for defect-free pixels, and using the reserved value and the converted zero crossing time for each pixel to generate a defect map array that uses a first color value for defective pixels and a second color value for defect-free pixels.

21. The method of claim 15, further comprising the step of generating a reference polynomial and subtracts the polynomial associated with each pixel in said portion of plurality of pixels from the reference polynomial to generate a contrast curve, wherein a peak in the contrast curve indicates the presence of a subsurface defect.

22. The method of claim 15, further comprising the step of fitting a first polynomial to a first portion of the data array and a second polynomial to a second portion of the data array.

23. The method of claim 15, further comprising the step of dividing the data array into an early region, an intermediate region, and a late region and fits a first polynomial to the early region, a second polynomial to the intermediate region, and a third polynomial to the late region.

24. The method of claim 15, further comprising the step of storing the coefficient array in a memory.

25. The method of claim 24, wherein the coefficient array is stored in the memory in a file having a size that is independent of the number of images obtained by the camera.

* * * * *